United States Patent
Li et al.

(10) Patent No.: US 12,343,362 B1
(45) Date of Patent: Jul. 1, 2025

(54) ***BACILLUS PROTEOLYTICUS* CWJ-2-GJ AND APPLICATION THEREOF**

(71) Applicant: NORTHEAST FORESTRY UNIVERSITY, Harbin (CN)

(72) Inventors: Dewen Li, Harbin (CN); Zhonghua Tang, Harbin (CN); Ying Liu, Harbin (CN); Xiaorui Guo, Harbin (CN); Zhonghua Zhang, Harbin (CN)

(73) Assignee: NORTHEAST FORESTRY UNIVERSITY, Harbin (CN)

( * ) Notice: Subject to any disclaimer, the term of this patent is extended or adjusted under 35 U.S.C. 154(b) by 0 days.

(21) Appl. No.: 18/963,644

(22) Filed: Nov. 28, 2024

(30) Foreign Application Priority Data

Dec. 29, 2023 (CN) .......................... 202311841059.9

(51) Int. Cl.
*A61K 35/74* (2015.01)
*C12N 1/20* (2006.01)
*C12R 1/07* (2006.01)

(52) U.S. Cl.
CPC .............. *A61K 35/74* (2013.01); *C12N 1/205* (2021.05); *C12R 2001/07* (2021.05)

(58) Field of Classification Search
CPC ..... A61K 35/74; C12N 1/205; C12R 2001/07
See application file for complete search history.

(56) References Cited

U.S. PATENT DOCUMENTS 5,385,837 A   1/1995   Boyer et al.

FOREIGN PATENT DOCUMENTS

| CN | 106367375 A | 2/2017 |
|----|-------------|--------|
| CN | 110172422 A | 8/2019 |
| CN | 112293127 A | 2/2021 |
| CN | 112899206 A | 6/2021 |
| CN | 114480219 A | 5/2022 |
| WO | 2014194117 A | 12/2014 |

OTHER PUBLICATIONS

English translation of CN112899206. (Year: 2021).*
Trinh et al., Root-associated bacteria Bacillus albus and Bacillus proteolyticus promote the growth of peanut seedlings and protect them from the aflatoxigenic Aspergillus flavus CDP2, Biocatalysis and Agricultural Biotechnology 47 (2023) 102582 (Year: 2023).*
Chen Shao-Xian, et al., Identification and enzymatic characteristics of a strain of Bacillus proteolyticus from olecranon peach, Feed Research, Dec. 31, 2021, pp. 79-84, vol. 16, doi: 10.13557/j.cnki.issn1002-2813.2021.16.018 Claims involved: 1-9 (abstract translated).

(Continued)

*Primary Examiner* — Robert B Mondesi
*Assistant Examiner* — Naghmeh Nina Moazzami
(74) *Attorney, Agent, or Firm* — Piloff Passino & Cosenza LLP; Rachel K. Piloff; Sean A. Passino

(57) ABSTRACT

A *Bacillus proteolyticus* CWJ-2-GJ and an application thereof are provided. The deposit number of the *Bacillus proteolyticus* CWJ-2-GJ is CGMCC No. 29159, and the *Bacillus proteolyticus* CWJ-2-GJ is isolated from the rhizosphere soil of *Acanthopanax senticosus*. The potted seedlings of *Acanthopanax senticosus* are irrigated with the bacterial liquid of the *Bacillus proteolyticus* CWJ-2-GJ.

3 Claims, 5 Drawing Sheets

Specification includes a Sequence Listing.

(56) References Cited

OTHER PUBLICATIONS

Piao Yang et al., Plant Growth Promotion and Stress Tolerance Enhancement through Inoculation with Bacillus proteolyticus OSUB18, Biology (Basel), Dec. 6, 2023, pp. 1-22, vol. 12, No. 1495 Claims involved: 1-9.
Retrieval report—First search dated Feb. 4, 2024 in SIPO application No. 202311841059.9.
Retrieval report—Supplementary search dated Feb. 21, 2024 in SIPO application No. 2023118410599.
Notification to Grant Patent Right for Invention dated Mar. 1, 2024 in SIPO application No. 202311841059.9.
Notice of first Office action dated Feb. 6, 2024 in SIPO application No. 202311841059.9.

* cited by examiner

SEQUENCE LISTING

```
Sequence total quantity: 2
SEQ ID NO: 1            moltype = DNA   length = 20
FEATURE                 Location/Qualifiers
source                  1..20
                        mol_type = other DNA
                        organism = synthetic construct
SEQUENCE: 1
agagtttgat cctggctcag                                              20

SEQ ID NO: 2            moltype = DNA   length = 17
FEATURE                 Location/Qualifiers
source                  1..17
                        mol_type = other DNA
                        organism = synthetic construct
SEQUENCE: 2
aaggaggtga tccagcc                                                 17
```

BACILLUS PROTEOLYTICUS CWJ-2-GJ AND APPLICATION THEREOF

CROSS-REFERENCE TO RELATED APPLICATIONS

This application claims priority to Chinese Patent Application No. 202311841059.9, filed on Dec. 29, 2023, the contents of which are hereby incorporated by reference.

INCORPORATION BY REFERENCE STATEMENT

This statement, made under Rules 77(b)(5)(ii) and any other applicable rule incorporates into the present specification of an XML file for a "Sequence Listing XML" (see Rule 831(a)), submitted via the USPTO patent electronic filing system or on one or more read-only optical discs (see Rule 1.52(e)(8)), identifying the names of each file, the date of creation of each file, and the size of each file in bytes as follows:

| File name: | PPH-US 22024-14806-SequenceListing.xml |
| --- | --- |
| Creation date: | Nov. 26, 2024 |
| Byte size: | 2,823 |

TECHNICAL FIELD

The present disclosure relates to the technical field of microorganisms, and in particular relates to a Bacillus proteolyticus CWJ-2-GJ and an application thereof.

BACKGROUND

Acanthopanax senticosus (Rupr.et Maxim.) Harms is an important Chinese herbal medicine in Chinese traditional medicine treasures, belonging to the Araliaceae Acanthopanax, which belongs to the same family as the well-known precious Chinese herbal medicine Ginseng, and is also called "Acanthopanax". The leaves, flowers, fruits and roots may all be used as medicine, with the functions of removing rheumatism, nourishing liver and kidney, strengthening body and reducing swelling. In recent years, there are many Chinese patent medicines with Acanthopanax senticosus as raw materials, and the demand of Acanthopanax senticosus in Chinese medicine prescriptions is also great, even expanding to health care products and alcohol industries. With the development of medicinal value of Acanthopanax senticosus, the wild resources of Acanthopanax senticosus are seriously insufficient, and Acanthopanax senticosus has been listed as a national third-class key protected species in 1987. Acanthopanax senticosus has been mainly used as medicine by roots and stems, and the resources of roots and stems are scarce, so people gradually began to study the feasibility of using leaves of Acanthopanax senticosus instead of roots and stems. Modern pharmacological research shows that leaves of Acanthopanax senticosus are relatively rich in resources and renewable, which are similar to most of the components in its roots and stems. Leaves of Acanthopanax senticosus have been used to develop food and health care products, and have certain clinical applications, which is a Chinese herbal medicine with great development value. Because the economic value of leaves of Acanthopanax senticosus has been greatly improved, it is particularly important to provide a cultivation method to improve the content of medicinal active substances in leaves of Acanthopanax senticosus.

Rhizosphere soil microorganisms are closely related to the growth and development, resistance, fecundity and productivity of plants, and occupy a certain niche in the soil, and are recognized as the second genome of plants with great potential in the development of green agriculture, and directly or indirectly participate in regulating the material circulation and energy flow in the soil. The core of rhizosphere microorganism is plant growth promoting rhizobacteria that is able to colonize extensively in the plant rhizosphere, effectively promote plant growth and development, and inhibit the growth of pathogenic bacteria. The plant growth promoting rhizobacteria is the link between plants and soil, constructing a healthy rhizosphere system through interaction with the soil and plants, and promoting plant production continuously and efficiently. With the steady increase of plant growth promoting rhizobacteria's potential in agriculture, more and more workers focus on the study of its molecular mechanism and the development and utilization of mature microbial agents and fertilizers, replacing the use of chemical fertilizers, pesticides and other supplements in a green and efficient way.

Based on this, it is of great significance to screen out excellent rhizosphere soil microorganisms with obvious growth promoting effect on Acanthopanax senticosus, and to develop efficient microbial agents and new bacterial fertilizers to promote the growth of Acanthopanax senticosus in the later stage.

SUMMARY

An objective of the present disclosure is to provide a Bacillus proteolyticus CWJ-2-GJ and an application thereof, so as to solve the problems existing in the prior art. The potted seedlings of Acanthopanax senticosus are irrigated with the bacterial liquid of Bacillus proteolyticus CWJ-2-GJ provided by the present disclosure, which may obviously promote the increase of the biomass of Acanthopanax senticosus and the yield of main medicinal ingredients in leaves, and effectively improve the planting benefit of Acanthopanax senticosus. At the same time, the method of promoting the growth of Acanthopanax senticosus by using the strain is simple in operation, low in cost and convenient for large-scale production management.

To achieve the above objectives, the present disclosure provides the following scheme.

The present disclosure provides a Bacillus proteolyticus CWJ-2-GJ, and a deposit number of the Bacillus proteolyticus CWJ-2-GJ is CGMCC No. 29159.

The present disclosure also provides a microbial preparation, and an active ingredient is the Bacillus proteolyticus CWJ-2-GJ.

In an embodiment, the microbial preparation also includes auxiliary materials.

The present disclosure also provides an application of the Bacillus proteolyticus CWJ-2-GJ or the microbial preparation in promoting accumulation of medicinal ingredients in leaves of Acanthopanax senticosus.

In an embodiment, the medicinal ingredients include Eleutheroside B, chlorogenic acid, Eleutheroside E and hyperoside.

The present disclosure also provides a method for promoting accumulation of medicinal ingredients in leaves of Acanthopanax senticosus, including a step of irrigating

*Acanthopanax senticosus* with a bacterial liquid of the *Bacillus proteolyticus* CWJ-2-GJ.

In an embodiment, an optical density (OD) value of the bacterial liquid at a wavelength of 600 nanometer (nm) is 0.8.

In an embodiment, an irrigation amount of the bacterial liquid is 200 millilitre per plant (mL/plant) each time, and irrigation is once every 7 days.

In an embodiment, the medicinal ingredients include Eleutheroside B, chlorogenic acid, Eleutheroside E and hyperoside.

The present disclosure also provides an application of the *Bacillus proteolyticus* CWJ-2-GJ or the microbial preparation in promoting growth of *Acanthopanax senticosus*.

The present disclosure discloses the following technical effects.

The present disclosure isolated a *Bacillus proteolyticus* CWJ-2-GJ from the rhizosphere soil of *Acanthopanax senticosus*, and found for the first time that the strain has the effect of increasing the yield of main medicinal ingredients in the leaves of *Acanthopanax senticosus*, thus promoting the application of rhizosphere soil microorganism of *Acanthopanax senticosus* in preparing *Acanthopanax senticosus* growth agents, providing stable and efficient strains and theoretical basis for further development of efficient microbial agents, and laying a foundation for later development of new bacterial fertilizers for promoting the growth of *Acanthopanax senticosus*.

Irrigating potted seedlings of *Acanthopanax senticosus* with the bacterial liquid of *Bacillus proteolyticus* provided by the present disclosure may obviously promote the increase of the biomass of *Acanthopanax senticosus* and the yield of main medicinal ingredients in leaves, and effectively improve the planting benefit of *Acanthopanax senticosus*. At the same time, the method of promoting the growth of *Acanthopanax senticosus* by using the strain is simple in operation, low in cost and convenient for large-scale production management.

BRIEF DESCRIPTION OF THE DRAWINGS

In order to explain the embodiments of the present disclosure or the technical solution in the prior art more clearly, the drawings needed in the embodiments will be briefly introduced below. Apparently, the drawings in the following description are only some embodiments of the present disclosure. For one of ordinary skill in the art, other drawings may be obtained according to these drawings without paying creative labor.

DETAILED DESCRIPTION OF THE EMBODIMENTS

Figure 1:
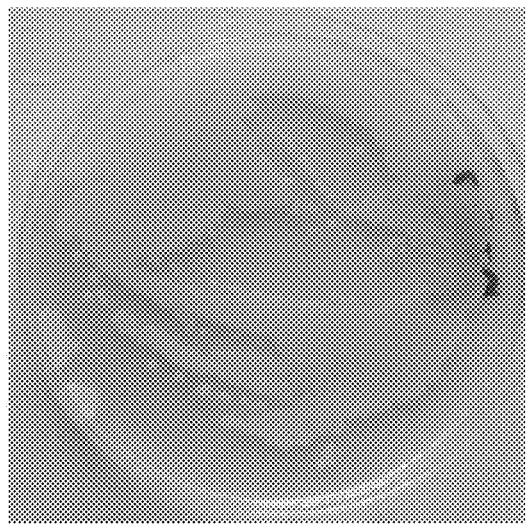
FIG. 1 is a colony diagram of pure culture of strain CWJ-2-GJ on Luria-Bertani (LB) medium.

A number of exemplary embodiments of the present disclosure will now be described in detail, and this detailed description should not be considered as a limitation of the present disclosure, but should be understood as a more detailed description of certain aspects, characteristics and embodiments of the present disclosure.

It should be understood that the terminology described in the present disclosure is only for describing specific embodiments and is not used for limiting the present disclosure. In addition, for the numerical range in the present disclosure, it should be understood that each intermediate value between the upper limit and the lower limit of the range is also specifically disclosed. Intermediate values within any stated value or stated range, as well as each smaller range between any other stated value or intermediate values within the stated range are also included in the present disclosure. The upper and lower limits of these smaller ranges may be independently included or excluded from the range.

Unless otherwise specified, all technical and scientific terms used herein have the same meaning as commonly understood by one of ordinary skill in the art to which the present disclosure relates. Although the present disclosure only describes the preferred methods and materials, any methods and materials similar or equivalent to those described herein may also be used in the practice or testing of the present disclosure. All documents mentioned in this specification are incorporated by reference to disclose and describe methods and/or materials related to the documents. In case of conflict with any incorporated document, the contents of this specification shall prevail.

It is obvious to those skilled in the art that many improvements and changes may be made to the specific embodiments of the present disclosure without departing from the scope or spirit of the present disclosure. Other embodiments will be apparent to the skilled person from the description of the present disclosure. The description and embodiments of that present disclosure are exemplary only.

The terms "comprising", "including", "having" and "containing" used herein are all open terms, which means including but not limited to.

Embodiment 1 Isolation, Purification and Identification of Strain

1. Isolation and Purification of Strain

In early May, during the growth of *Acanthopanax senticosus*, plants with good growth were selected, the soil at the edge of the pot was removed, the roots were dug out with a medicine spoon, the roots were put into a sterile sealing bag, the soil on the roots was gently shaken off, 1 gram (g) of rhizosphere soil of *Acanthopanax senticosus* was weighed with a balance, the weighed soil sample was put into a beaker filled with sterile glass beads and 99 millilitre (mL) of sterile water in an ultra-clean workbench, and placed at 37° C. The beaker was shaken for 90 minutes (min) on a shaking table with a rotating speed of 120 revolutions per minute (r/min) to fully mix the mixture, and was allowed to stand for 5 min. In the ultra-clean workbench, 1 mL of soil suspension was sucked with a pipette gun and added into a centrifuge tube filled with 9 mL of sterile water, and thoroughly mixed. According to this method, the soil suspension was diluted into soil suspension with a gradient of $10^{-3}$-$10^{-7}$ in turn.

10 microliter (μL) of soil suspension with a concentration gradient of $10^{-6}$ was respectively absorbed into LB solid medium plates prepared in advance, spread evenly with a coating rod that had been sterilized; 5-10 repetitions were set, and the evenly coated plates were put in a constant temperature incubator at 37° C. for inverted cultivation for 36 hours (h).

The growth of colonies in the plates was observed, and colonies with obvious differences with large morphology and good growth were selected. Pure culture was carried out in LB medium by streak method, purification culture was carried out for many times, and observation was performed under a microscope until a single colony is confirmed to be free of miscellaneous bacteria, and the purified rhizosphere soil microorganism of Acanthopanax senticosus-strain CWJ-2-GJ, No. 2-1 was obtained.

2. Identification of Strain

Figure 2:
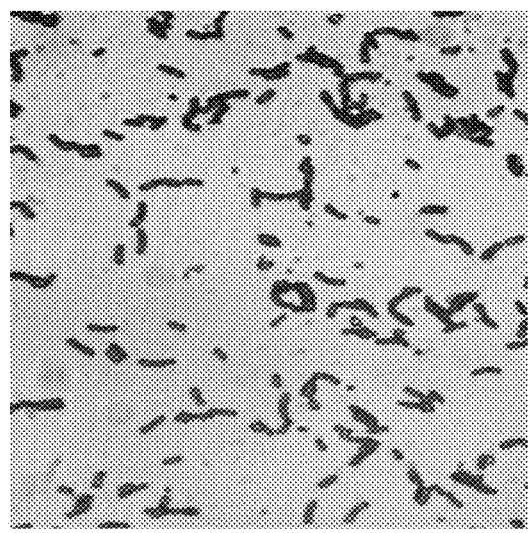
FIG. 2 is a diagram of a Gram staining result of strain CWJ-2-GJ.

The colony of strain CWJ-2-GJ was identified by morphology: smooth surface, irregular shape, irregular edge, sticky, white and opaque (FIG. 1). The Gram staining result showed Gram-positive bacteria (FIG. 2).

The strain of the purified rhizosphere soil microorganism of Acanthopanax senticosus was inoculated in LB liquid culture medium, cultured for 18 h at 37° C. and 200 r/min in a shaking table, and the bacteria were collected by centrifugation. The genomic DNA was extracted by protease K cleavage, and the genomic DNA was used as a template for polymerase chain reaction (PCR) amplification with 16S rDNA universal primers.

```
Upstream primer:
                                SEQ ID NO. 1
5'-AGAGTTTGATC-CTGGCTCAG-3',;

downstream primer:
                                SEQ ID NO. 2
5'-AAGGAGGTGATCCAGCC-3',.
```

PCR amplification system: 5×Buffer 10 μL, deoxy-ribonucleoside triphosphate (dNTP) (10 millimole (mM)) 1 μL, upstream and downstream primers 1 μL each, DNA template 1-3 μL, Thermus aquaticus (Taq) DNA polymerase 1 μL, supplemented with double distilled water (ddH$_2$O) to 50 μL.

PCR reaction conditions: pre-denaturation at 94° C. for 2 min, denaturation at 94° C. for 30 seconds (s), annealing at 56° C. for 30 s, extension at 72° C. for 1.5 min, cyclic amplification for 27 times, extension at 72° C. for 5 min, and finally heat preservation at 10° C.

Figure 3:
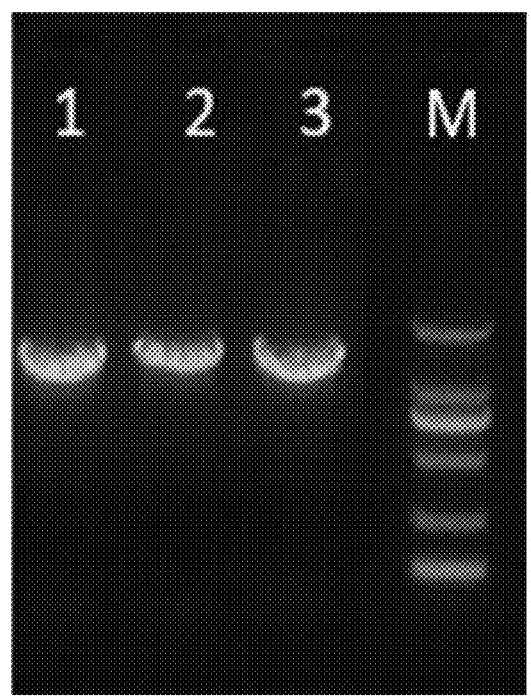
FIG. 3 is an agarose gel electrophoresis diagram of amplification products of strain CWJ-2-GJ, where a lane M is DL2000Marker, and bands from top to bottom are 2000 base pair (bp), 1000 bp, 750 bp, 500 bp, 250 bp and 100 bp; lanes 1-3 are the amplification products of strain CWJ-2-GJ.

The amplification products were amplified into a single band by gel electrophoresis, and the band was clear and the size was about 1500 bp (FIG. 3).

Figure 4:
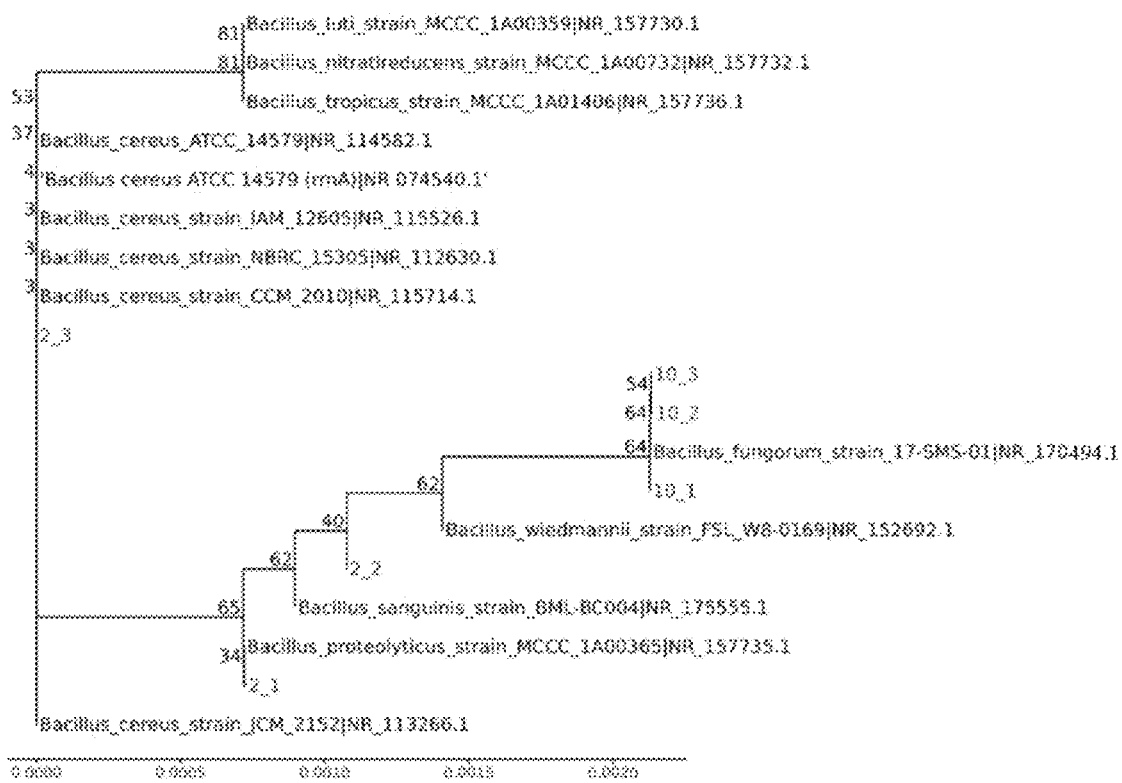
FIG. 4 is a phylogenetic tree diagram of strain CWJ-2-GJ.

After the amplification products were recovered and purified, and were entrusted to Shanghai TinyGene Bio-Tech Co., Ltd for sequencing. The homology of sequencing results with Bacillus sp. MCCC 1A00365 was 100% by 16SrDNA sequence alignment (NCBI database). The phylogenetic tree constructed is shown in FIG. 4. Combined with the identification of microbial morphology, physiological and biochemical indexes, strain CWJ-2-GJ was identified as Bacillus proteolyticus, and the obtained single colony was preserved with glycerol.

3. Biological Deposit

Strain CWJ-2-GJ was deposited in the general microbiology center of China microbiological culture collection management Committee on Nov. 27, 2023, with the deposit number of CGMCC No. 29159, and the deposit address is the institute of microbiology of China academy of sciences, No. 3, No. 1 courtyard, Beichen west road, Chaoyang district, Beijing.

Embodiment 2 Growth Promoting Effect of the Strain on Acanthopanax senticosus

1. Cultivation of Rhizosphere Soil Microorganism of Acanthopanax senticosus.

Under aseptic conditions, a small number of colonies of strain CWJ-2-GJ were picked up by inoculation needle, inoculated in sterilized LB solid medium, and activated and cultured for 1-3 days at 37° C.

The activated strain CWJ-2-GJ was replanted in LB liquid culture medium, and was placed on a shaking table at 37° C. with a rotation speed of 200 r/min for propagation and culture. During this period, the absorbance of the bacterial liquid was measured at the wavelength of 600 nanometer (nm), and the culture was stopped when the OD value of the bacterial liquid reached 0.8.

2. Pot Experiment for Promoting Growth

Potted seedlings of Acanthopanax senticosus were irrigated with bacterial liquid obtained after propagation and culture (rhizosphere microorganism group), and the same amount of clean water was irrigated as control (CK), with 10 pots of each treatment repeated, and each pot of plants was irrigated with 200 mL of bacterial liquid once a week (7 days), and the irrigating time was from 4 pm to 6 pm.

After 60 days, the leaves were harvested, and the growth indexes such as plant height, leaf area, leaf thickness and leaf fresh weight of Acanthopanax senticosus were measured. The data were analyzed by using the multivariate analysis of variance module of statistical software Statistical Product and Service Solutions (SPSS), and P<0.05 indicated that the difference was statistically significant. The results are shown in Table 1.

TABLE 1

Effects of rhizosphere microorganism treatment on growth indexes of Acanthopanax senticosus

| Treatment number | Plant height | Leaf thickness (mm) | Leaf area (cm$^2$) | Fresh weight (g) |
|---|---|---|---|---|
| Rhizosphere microorganism | 3.56 ± 0.13a | 0.32 ± 0.26a | 144.21 ± 0.29a | 1.37 ± 0.03a |
| CK | 2.21 ± 0.15b | 0.31 ± 0.26a | 126.94 ± 0.27b | 1.23 ± 0.03b |

Note:
lowercase letters indicate a significant level difference of 0.05, and the same letters in the same column indicate that the difference has not reached a significant level.

Note: lowercase letters indicate a significant level difference of 0.05, and the same letters in the same column indicate that the difference has not reached a significant level.

As may be seen from Table 1, the plant height of Acanthopanax senticosus in the control group increased by 2.21 centimeter (cm), the leaf thickness was 0.31 millimeter (mm), the leaf area was 126.94 square centimeter (cm$^2$), and the leaf fresh weight was 1.23 g; the plant height of Acanthopanax senticosus in rhizosphere microorganism treatment group was 3.56 cm, the leaf thickness was 0.32 mm, the leaf area was 144.21 cm$^2$, and the leaf fresh weight was 1.37 g. The bacterial liquid of strain CWJ-2-GJ was used to irrigate potted seedlings of Acanthopanax senticosus, resulting in a 1.6-fold increase in plant height of the potted seedlings, a 1.03-fold increase in leaf thickness, and a 1.1-fold increase in leaf area and fresh weight, fully proving that the method of symbiosis between strain CWJ-2-GJ and potted seedlings of Acanthopanax senticosus may significantly promote the growth of potted seedlings of Acanthopanax senticosus.

3. Determination of Main Medicinal Ingredients in Leaves

The content of the main medicinal ingredients in the leaves of *Acanthopanax senticosus* was determined by high performance liquid chromatography, and the data were analyzed by the multivariate analysis of variance module of statistical software SPSS, and P<0.05 indicated statistically significant differences. The results are shown in FIG. 5.

Figure 5:
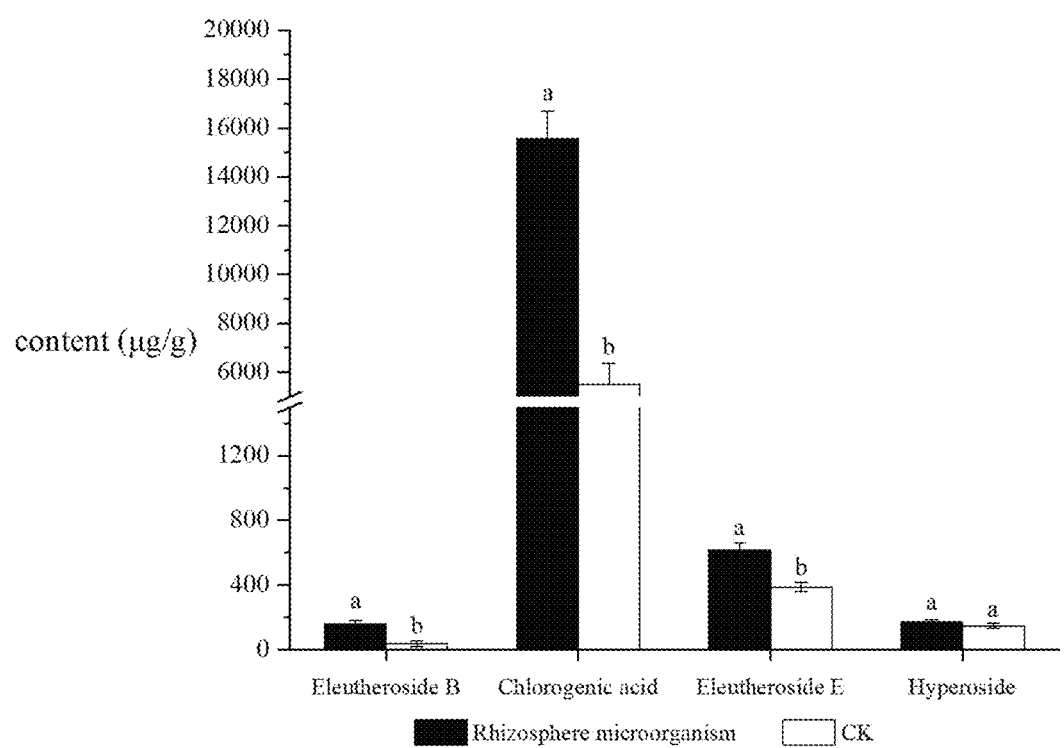
FIG. 5 shows effects of bacterial liquid treatment of strain CWJ-2-GJ on the contents of main medicinal ingredients in leaves of *Acanthopanax senticosus*.

As may be seen from FIG. 5, the content of Eleutheroside B, the main medicinal ingredient in the leaves of the control group, is 44.86 microgram per gram (μg/g), the content of chlorogenic acid is 5935.10 μg/g, the content of Eleutheroside E is 235.92 μg/g, and the content of hyperoside is 159.82 μg/g. The content of Eleutheroside B, the main medicinal ingredient in the leaves of rhizosphere microorganism treatment group, is 160.66 μg/g, the content of chlorogenic acid is 16530.39 μg/g, the content of Eleutheroside E is 489.64 μg/g, and the content of hyperoside is 176.60 μg/g. The bacterial liquid of strain CWJ-2-GJ was used to irrigate potted seedlings of *Acanthopanax senticosus*, resulting in a 3.5-fold increase in the content of Eleutheroside B, a 2.8-fold increase in chlorogenic acid content, a 2.1-fold increase in the content of Eleutheroside E, and a 1.1-fold increase in the content of hyperoside in the leaves of the potted seedlings, which was much higher than the control group irrigated with water.

The present disclosure fully proves that the method of symbiosis between strain CWJ-2-GJ, the rhizosphere soil microorganism of *Acanthopanax senticosus*, and the potted seedlings of *Acanthopanax senticosus* has obvious effects of promoting the growth of *Acanthopanax senticosus* and promoting the content accumulation of main medicinal ingredients in leaves of *Acanthopanax senticosus*, and may be applied to the cultivation of *Acanthopanax senticosus* and improve the economic benefits of *Acanthopanax senticosus* cultivation at the same time. Rhizosphere soil microorganism of *Acanthopanax senticosus*, especially strain CWJ-2-GJ isolated by the present disclosure, may be used to prepare medicines for promoting the growth of *Acanthopanax senticosus*.

The above-mentioned embodiments only describe the preferred mode of the present disclosure, and do not limit the scope of the present disclosure. Under the premise of not departing from the design spirit of the present disclosure, various modifications and improvements made by ordinary technicians in the field to the technical scheme of the present disclosure shall fall within the protection scope determined by the claims of the present disclosure.

What is claimed is:

1. A method for increasing the biomass and accumulation of medicinal ingredients in leaves of *Acanthopanax senticosus*, comprising a step of irrigating *Acanthopanax senticosus* with a bacterial liquid of *Bacillus proteolyticus* CWJ-2-GJ, wherein a deposit number of the *Bacillus proteolyticus* CWJ-2-GJ is CGMCC No. 29159; wherein the irrigation promotes the biomass growth and increases the yield of the medicinal ingredients Eleutheroside B, chlorogenic acid, Eleutheroside E, and hyperoside in the leaves.

2. The method according to claim 1, wherein an OD value of the bacterial liquid at a wavelength of 600 nm is 0.8.

3. The method according to claim 2, wherein an amount of bacterial liquid for irrigation is 200 mL/plant, and irrigation occurs once every 7 days.

* * * * *